United States Patent
Georgescu et al.

(10) Patent No.: US 10,108,779 B2
(45) Date of Patent: Oct. 23, 2018

(54) AUTOMATIC NUCLEAR SEGMENTATION

(71) Applicant: LEICA BIOSYSTEMS IMAGING, INC., Vista, CA (US)

(72) Inventors: Walter Georgescu, San Marcos, CA (US); Kiran Saligrama, San Diego, CA (US); Allen Olson, San Diego, CA (US); Bharat Annaldas, Oceanside, CA (US)

(73) Assignee: LEICA BIOSYSTEMS IMAGING, INC., Vista, CA (US)

( * ) Notice: Subject to any disclaimer, the term of this patent is extended or adjusted under 35 U.S.C. 154(b) by 0 days.

(21) Appl. No.: 15/517,489

(22) PCT Filed: Dec. 12, 2016

(86) PCT No.: PCT/US2016/066200
§ 371 (c)(1),
(2) Date: Apr. 6, 2017

(87) PCT Pub. No.: WO2017/106106
PCT Pub. Date: Jun. 22, 2017

(65) Prior Publication Data
US 2017/0300617 A1    Oct. 19, 2017

Related U.S. Application Data

(60) Provisional application No. 62/267,775, filed on Dec. 15, 2015.

(51) Int. Cl.
*G06F 19/24* (2011.01)
*G06K 9/62* (2006.01)
(Continued)

(52) U.S. Cl.
CPC .......... *G06F 19/24* (2013.01); *G06K 9/0014* (2013.01); *G06K 9/62* (2013.01); *G06K 9/80* (2013.01);
(Continued)

(58) Field of Classification Search
CPC . G06F 19/24; G06K 9/62; G06K 9/80; G06K 9/0014; G06K 9/00; G06T 2207/30024; G06T 7/62; G06T 7/11
See application file for complete search history.

(56) References Cited

U.S. PATENT DOCUMENTS

2013/0230230 A1\*  9/2013  Ajemba ............... G06T 7/0012
                                                        382/133
2015/0213598 A1   7/2015  Madabhushi et al.
(Continued)

OTHER PUBLICATIONS

International Search Report and Written Opinion dated Feb. 27, 2017 issued by the United States Patent Office in counterpart International Application No. PCT/US2016/66200, 8 pages.
(Continued)

*Primary Examiner* — Yon Couso
(74) *Attorney, Agent, or Firm* — Procopio, Cory, Hargreaves & Savitch LLP

(57) ABSTRACT

Automatic nuclear segmentation. In an embodiment, a plurality of superpixels are determined in a digital image. For each of the superpixels, any superpixels located within a search radius from the superpixel are identified, and, for each unique local combination between the superpixel and any identified superpixels located within the search radius from the superpixel, a local score for the local combination is determined. One of a plurality of global sets of local combinations with an optimum global score is identified based on the determined local scores.

18 Claims, 5 Drawing Sheets

(51) Int. Cl.
*G06K 9/80* (2006.01)
*G06T 7/11* (2017.01)
*G06T 7/62* (2017.01)
*G06K 9/00* (2006.01)

(52) U.S. Cl.
CPC .................. *G06T 7/11* (2017.01); *G06T 7/62* (2017.01); *G06K 9/00* (2013.01); *G06T 2207/30024* (2013.01)

(56) References Cited

U.S. PATENT DOCUMENTS

2017/0243051 A1* 8/2017 Chukka .............. G06K 9/00147
2017/0372117 A1* 12/2017 Bredno ................ G06K 9/0014

OTHER PUBLICATIONS

Ushizima et al., Segmentation of subcellular compartments combining superpixel representation with voronoi diagrams, Overlapping Cervical Cytology Image Segmentation Challenge—IEEE International Symposium on Biomedical Imaging, Apr. 2014.

Zhang et aL, Cell Detection and Segmentation using Correlation Clustering, International Conference on Medical Image Computing and Computer-Assisted Intervention, Sep. 2014, Springer International Publishing.

Schüffler et al., TMARKER: A free software toolkit for histopathological cell counting and staining estimation, Journal of pathology informatics, 4(2), Jan. 1, 2014.

* cited by examiner 4.07        2.85

Search Radius R

Search Radius R

AUTOMATIC NUCLEAR SEGMENTATION

CROSS-REFERENCE TO RELATED APPLICATIONS

This application is the National Stage of PCT/US2016/066200, filed on Dec. 12, 2016 claims priority to U.S. Provisional Patent App. No. 62/267,775, filed on Dec. 15, 2015, each of which is hereby incorporated herein by reference in its entirety.

BACKGROUND

Field of the Invention

The embodiments described herein are generally directed to automatic segmentation in digital imaging, and in one embodiment, to automatic nuclear segmentation in digital pathology.

Description of the Related Art

In segmentation tasks for identifying objects in digital images, it is often advantageous to operate at a higher level than that of individual pixels. This can be accomplished by clustering individual pixels into entities, called "superpixels," according to similarity rules. Because the number of superpixels is much smaller than the original number of pixels in the image, subsequent operations on the superpixels can be performed much faster and with lower memory requirements than operations on the individual pixels.

This clustering task may be accomplished, with varying degrees of success, using dedicated superpixel algorithms, or by setting normal segmentation algorithms to over-segment. Examples of dedicated superpixel algorithms include:

Quick Shift, described in "Quick shift and kernel methods for mode seeking" by Vedaldi et al., Lecture Notes in Computer Science (including its subseries Lecture Notes Artificial Intelligence and Lecture Notes in Bioinformatics), vol. 5305 LNCS, no. PART 4, pp. 705-718 (2008), which is hereby incorporated herein by reference;

Superpixels Extracted via Energy-Driven Sampling (SEEDS), described in "SEEDS: Superpixels Extracted via Energy-Driven Sampling" by Van Den Bergh et al. (2013), which is hereby incorporated herein by reference; and Simple Linear Iterative Clustering (SLIC) Superpixels, described in "SLIC superpixels compared to state-of-the-art superpixel methods" by Achanta et al., IEEE Transactions on Pattern Analysis and Machine Intelligence, vol. 34, no. 11, pp. 2274-81 (2012), which is hereby incorporated herein by reference.

An example of a normal segmentation algorithm is the watershed algorithm, described in "Watersheds in digital spaces: an efficient algorithm based on immersion simulations" by Vincent et al., IEEE Transactions on Pattern Analysis and Machine Intelligence, vol. 13 (1991), which is hereby incorporated by reference.

Typically, the ultimate goal in segmentation is to identify objects present in the image being segmented. In superpixel-based segmentation, this goal has been traditionally accomplished by clustering the individual superpixels into objects using a clustering algorithm, such as hierarchical clustering. Hierarchical clustering is described in "Learning to agglomerate superpixel hierarchies" by Jain et al., Advances in Neural Information Processing Systems, pp. 1-9 (2011), and "Machine Learning of Hierarchical Clustering to Segment 2D and 3D images" by Nunez-Iglesias et al., Public Library of Science (PLoS) One, vol. 8, no. 8 (2013), which are hereby incorporated herein by reference. Hierarchical clustering joins superpixels that are similar to each other into objects, similarly to the way individual pixels are joined into superpixels. However, this approach will fail for objects which can only be properly clustered by joining dissimilar superpixels.

SUMMARY

Embodiments are disclosed for automatic nuclear segmentation.

In an embodiment, a method is disclosed. The method comprises using at least one hardware processor to: determine a plurality of superpixels in a digital image; for each of the plurality of superpixels, identify any superpixels located within a search radius from the superpixel, and, for each unique local combination between the superpixel and any identified superpixels located within the search radius from the superpixel, determine a local score for the local combination; and identify one of a plurality of global sets of local combinations with an optimum global score based on the determined local scores.

In another embodiment, a system is disclosed. The system comprises: at least one hardware processor; and one or more software modules that, when executed by the at least one hardware processor, determine a plurality of superpixels in a digital image, for each of the plurality of superpixels, identify any superpixels located within a search radius from the superpixel, and, for each unique local combination between the superpixel and any identified superpixels located within the search radius from the superpixel, determine a local score for the local combination, and identify one of a plurality of global sets of local combinations with an optimum global score based on the determined local scores.

In another embodiment, a non-transitory computer-readable medium having instructions stored thereon is disclosed. The instructions, when executed by a processor, cause the processor to: determine a plurality of superpixels in a digital image; for each of the plurality of superpixels, identify any superpixels located within a search radius from the superpixel, and, for each unique local combination between the superpixel and any identified superpixels located within the search radius from the superpixel, determine a local score for the local combination; and identify one of a plurality of global sets of local combinations with an optimum global score based on the determined local scores.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Embodiments of systems, methods, and non-transitory computer-readable media are disclosed for automatic nuclear segmentation. Advantageously, certain embodiments can accurately combine superpixels, regardless of whether they are similar or dissimilar, using, for example, machine-learning techniques and global optimization. While these embodiments are disclosed in the context of nuclear segmentation, they may be adapted for other types of object segmentation.

After reading this description, it will become apparent to one skilled in the art how to implement alternative embodiments and alternative applications. However, although various embodiments will be described herein, it is understood that these embodiments are presented by way of example and illustration only, and not limitation. As such, this detailed description of various embodiments should not be construed to limit the scope or breadth of the present application as set forth in the appended claims.

1. Process Overview

Embodiments of processes for automatic nuclear segmentation will be described in detail. It should be understood that the described processes may be embodied in one or more software modules that are executed by one or more hardware processors. The described processes may be implemented as instructions represented in source code, object code, and/or machine code. These instructions may be executed directly by hardware processor(s), or alternatively, may be executed by a virtual machine operating between the object code and hardware processor(s).

Figure 1:
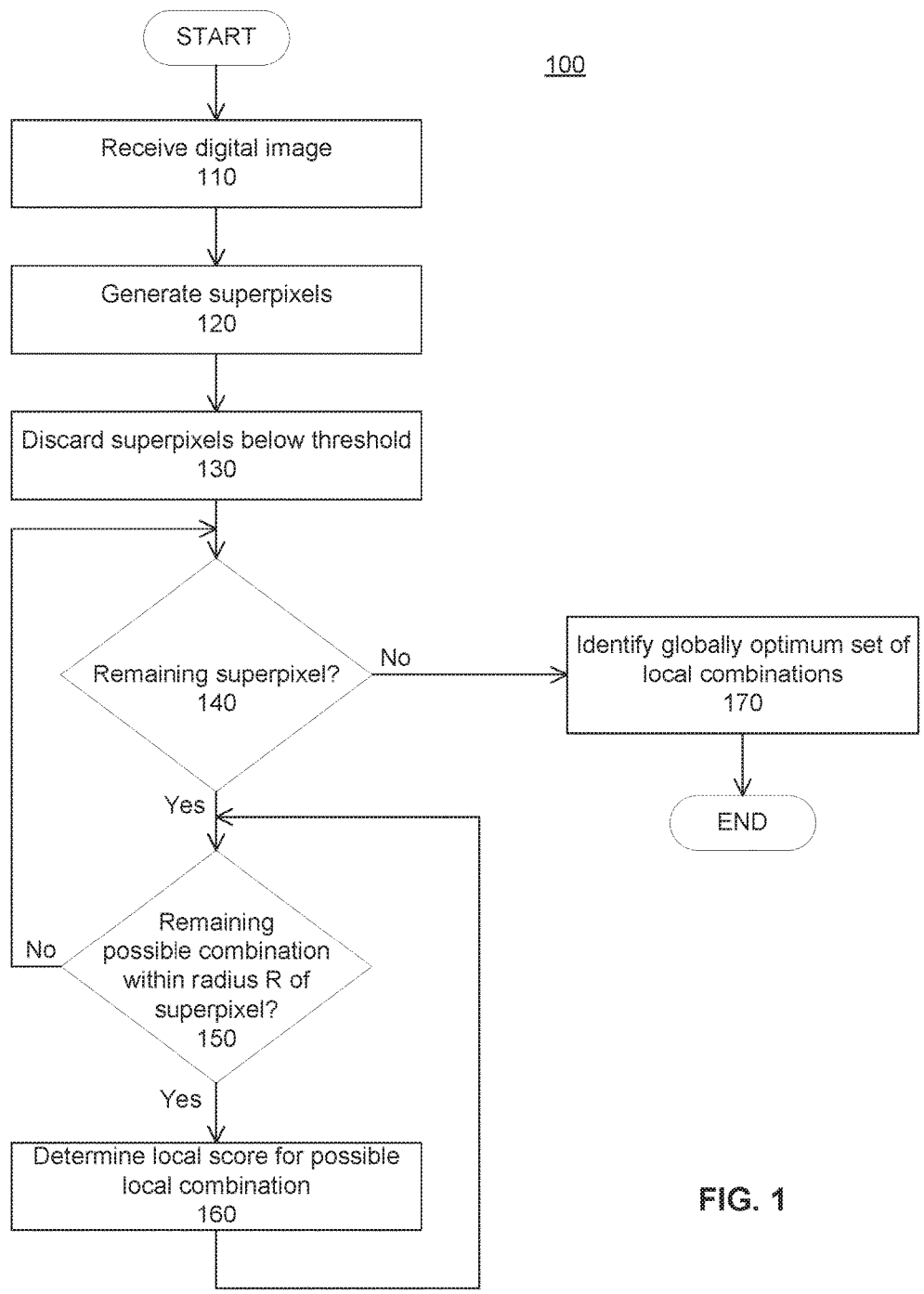
FIG. 1 illustrates a process of automatic nuclear segmentation, according to an embodiment.

FIG. 1 illustrates a process 100 of automatic nuclear segmentation, according to an embodiment. Beginning in step 110, a digital image is received. It should be understood that the digital image may be received by any means. For example, the digital image may be retrieved or otherwise received from a local memory, or retrieved or otherwise received from a remote system over one or more networks using standard communication protocols. The digital image may be acquired locally or remotely, contemporaneously or not contemporaneously, by an image acquisition device, such as a slide scanner, and may comprise an image of a specimen, such as a pathology specimen (e.g., imaged using fluorescence or other illumination).

1.1. Superpixel Generation

In step 120, superpixels are generated for the digital image. In an embodiment, each pixel in the digital image is assigned to a superpixel. The superpixels may be generated using the Quick Shift algorithm, SEEDS algorithm, SLIC Superpixels algorithm, or watershed algorithm configured for over-segmentation, as discussed above. However, in a preferred embodiment for nuclear segmentation, superpixels are generated using a curvature segmentation technique. Curvature segmentation techniques tend to generate types of superpixels that are well-suited for nuclear segmentation.

In an embodiment of a curvature segmentation technique, a curvature image is approximated from a smoothed version of the original image as:

$$\frac{\partial I}{\partial x^2} + \frac{\partial I}{\partial y^2} + \sqrt{\left(\frac{\partial I}{\partial x^2} - \frac{\partial I}{\partial y^2}\right)^2 + \left(\frac{\partial I}{\partial xy}\right)^2}$$

where $$\frac{\partial I}{\partial x^2} = I(x+1, y) + I(x-1, y) - 2 * I(x, y),$$

$$\frac{\partial I}{\partial y^2} = I(x, y+1) + I(x, y-1) - 2 * I(x, y),$$

$$\frac{\partial I}{\partial xy} = I(x-1, y-1) + I(x+1, y+1) - I(x-1, y+1) - I(x+1, y-1),$$

and $I(x, y)$ is the intensity value at coordinates x,y of the smoothed image. The areas of high positive curvature in the image are used to mark the boundaries of superpixels. These boundaries define an over-segmentation of the objects (e.g., nuclei) and the background.

Once the digital image has been segmented into superpixels, in step 130, background superpixels (i.e., superpixels which are likely of no interest, for example, because they are unlikely to represent any portion of an object of interest) may be discarded. These background superpixels may be discarded using a local thresholding technique.

In an embodiment of the local thresholding technique, a difference of Gaussians (DoG) technique is used as a blob detector to separate objects (e.g., nuclei) from background superpixels. However, any type of local thresholding technique may be used to achieve the same or similar result. In the DoG technique, a scaled-down version of the image is smoothed with two Gaussians kernels of different width. Positive pixels in the difference image are used as a mask to identify superpixels representing an object (e.g., nucleus). Mathematically, the DoG operation can be summarized as:

$$D = I(x, y) * \frac{1}{2\pi\sigma_1^2} e^{-(x^2+y^2)/(2\sigma_1^2)} - I(x, y) * \frac{1}{2\pi\sigma_2^2} e^{-(x^2+y^2)/(2\sigma_2^2)},$$

wherein $\sigma_1^2$, $\sigma_2^2$ are the variances of the two Gaussian functions.

The result of the thresholding technique is that each pixel within an object of interest in the digital image will be assigned to a superpixel, such that each superpixel represents at least a portion of an object of interest, and each object of interest is comprised of one or more superpixels. It should be understood that, in step 130, methods, other than the thresholding technique, may be used, instead of or in addition to the thresholding technique, to reduce the number of superpixels that must be considered in the subsequent steps of process 100.

Figure 2A:
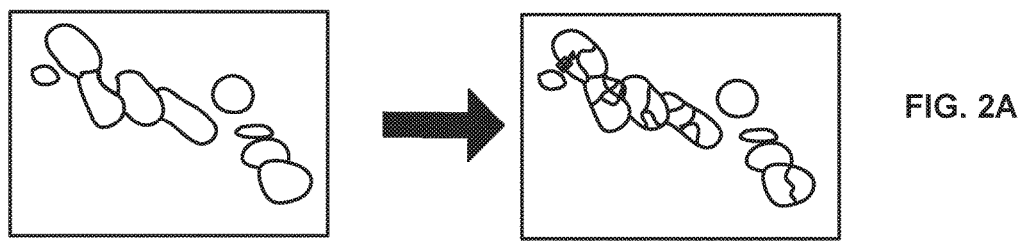
FIG. 2A illustrates an example of superpixel generation, according to an embodiment.

FIG. 2A illustrates an example of superpixel generation, according to an embodiment. Specifically, a digital image of cell nuclei in the left-most image is segmented into superpixels, as shown in the right-most image. As illustrated, some of these superpixels may represent a portion of a cell nucleus, whereas other ones of these superpixels may represent an entire cell nucleus. Thus, after superpixel generation, each cell nucleus in the digital image is represented by one or more superpixels that have not been discarded by the thresholding and/or other techniques in step 130.

1.2. Machine Learning

In an embodiment, a machine learning algorithm may be trained to predict whether or not a particular combination of superpixels is likely to represent an object of interest (e.g., a cell nucleus). The machine learning algorithm may be trained using a set of annotated test images. For example, experts may identify objects (e.g., nuclei) in a set of test images by annotating them, for example, by drawing outlines around each object or otherwise delineating each object in each of the test images in the set. In embodiments designed for nuclear segmentation, the set of test images may comprise different types of nuclei (e.g., fluorescently-labeled nuclei) imaged at a range of densities (i.e., a plurality of densities) and a range of optical magnifications (i.e., a plurality of optical magnifications).

Steps 110-130 may be applied to each annotated image in the set of test images to generate a plurality of superpixels for each annotated image. For each annotated image, process 100 iterates through steps 140-160 for each of the superpixels remaining after step 130, i.e., until all of the superpixels have been considered. Furthermore, process 100 iterates through steps 150 and 160 for each possible combination of the current superpixel under consideration with superpixel(s) within a search radius R of the current superpixel. Any possible combination of the current superpixel with one or more superpixels within search radius R of the current superpixel may be referred to herein as a "local combination." In an embodiment, a local combination, as used herein, may also include the current superpixel in isolation, i.e., without being combined with any superpixels within search radius R of the current superpixel.

In step 140, it is determined whether or not any superpixels remain to be considered. In this manner, process 100 may consider every superpixel that remains after step 130. Once all of the superpixels have been considered (i.e., "No" at step 140), process 100 proceeds to step 170. Otherwise (i.e., "Yes" at step 140), process 100 assigns the next superpixel to consider as the current superpixel and proceeds to step 150.

In step 150, it is determined whether or not any possible local combinations remain for the current superpixel. In this manner, process 100 may consider every possible local combination for every superpixel remaining after step 130. However, for efficiency, redundant or non-unique combinations of superpixels may be discarded. For example, if the combination of superpixel A with superpixel B has been considered during the iteration for superpixel A, it is not necessary to subsequently consider the combination of superpixel B with superpixel A during the iteration for superpixel B. Once all of the unique possible local combinations (i.e., within search radius R of the current superpixel) have been considered (i.e., "No" at step 150), process 100 returns to step 140. Otherwise (i.e., "Yes" at step 150), process 100 determines the next possible local combination to consider for the current superpixel and proceeds to step 160.

In an embodiment, search radius R is a radius from the center of the current superpixel. Furthermore, in an embodiment, search radius R is set based on an expected radius or diameter of nuclei in the digital image received in step 110 and/or a resolution or zoom level of the digital image received in step 110. For example, search radius R may be set to twice the expected diameter of the nuclei of interest in the digital image. This may ensure that all possible combinations of superpixels that could feasibly represent nuclei are considered, even when the sizes of the nuclei in the digital image vary widely. However, it should be understood that this is simply one example, and that search radius R may be set according to the design goals of any particular implementation. In addition, search radius R may be a system-specified or user-specified value (e.g., input by a user via a user interface), or may be based on a system-specified or user-specified value (e.g., a multiple of the system-specified or user-specified value for an expected nuclear radius or diameter, or otherwise derived from the expected nuclear radius or diameter). Search radius R may also be converted from one metric (e.g., μm) to a number of pixels, based on the resolution or zoom level of the digital image (which may be a user-specified setting, system setting, parameter received with the digital image or retrieved from the metadata of the digital image, etc.). In this manner, search radius R may be represented by a number of pixels from the current superpixel under consideration.

Figure 3A:
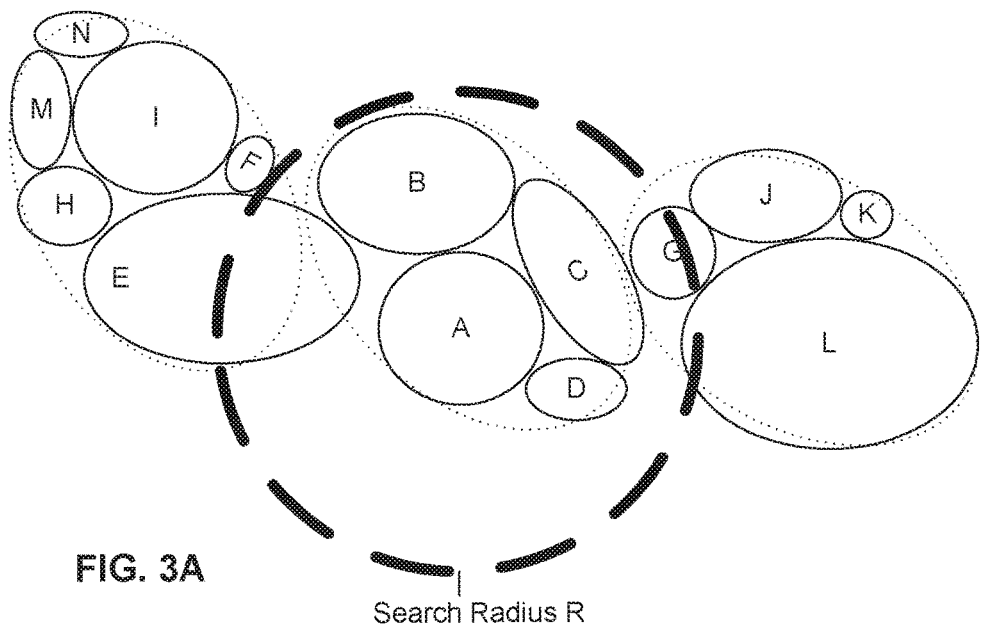
FIGS. 3A and 3B illustrate an example of how possible superpixel combinations may be chosen in accordance with a search radius, according to an embodiment.
Figure 3B:
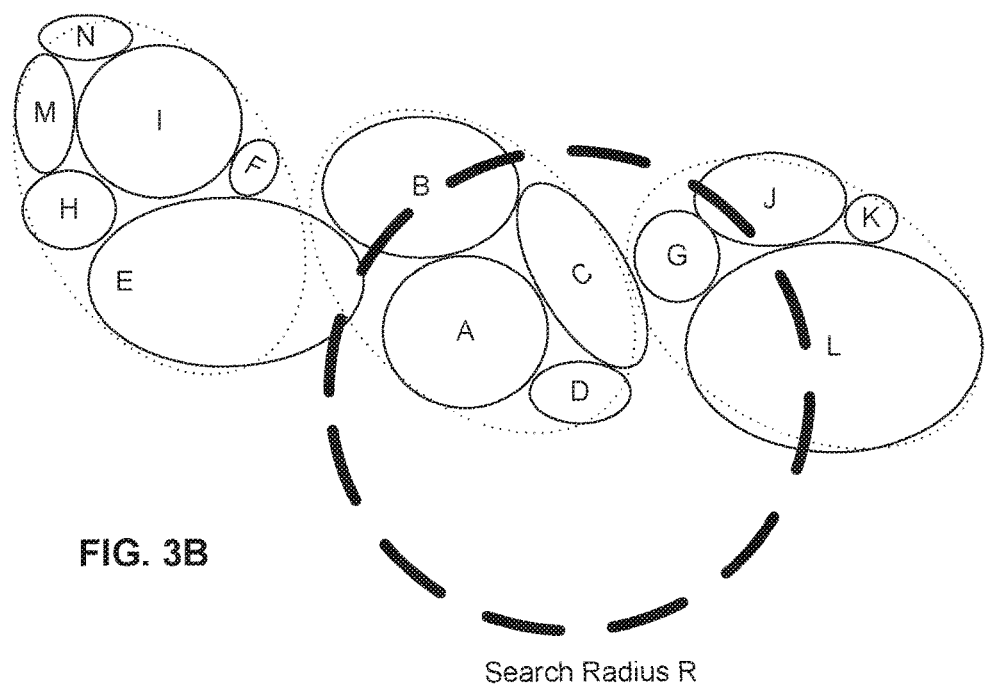

FIGS. 3A and 3B illustrate an example of how possible superpixel combinations may be determined in accordance with a search radius R, according to an embodiment. In each of FIGS. 3A and 3B, the light dotted lines represent objects (e.g., nuclei) in a digital image, the thick dashed line represents search radius R, and each of the labeled solid-lined ellipses represents a superpixel. In FIG. 3A, superpixel A, at the center of search radius R, represents the current superpixel selected in step 140, whereas in FIG. 3B, superpixel D, at the center of search radius R, represents the current superpixel selected in step 140.

In an embodiment, all superpixels that are at least partially within search radius R are considered for possible combination with the current superpixel under consideration. In such an embodiment, in FIG. 3A, in which superpixel A is the current superpixel, superpixels B, C, D, E, and G would be considered for possible combination with superpixel A, since all of these superpixels are at least partially within search radius R. In FIG. 3B, in which superpixel D is the current superpixel, superpixels A, B, C, E, G, J, and L would be considered for possible combination with superpixel D, since all of these superpixels are at least partially within search radius R. In different implementations, a superpixel may be at least partially within search radius R if any portion of it is within search radius R, if a certain percentage of it is within search radius R, if a center of the superpixel is within search radius R, etc.

In an alternative embodiment, only superpixels that are wholly within search radius R are considered for possible combination with the current superpixel under consideration. Referring to FIG. 3A, in which superpixel A is the current superpixel, in such an embodiment, superpixels B, C, and D would be considered for possible local combination with superpixel A since these superpixels are wholly within search radius R, whereas superpixels E and G would not be considered for possible local combination since these superpixels are only partially within search radius R. In this embodiment, each of the following unique local combinations would be considered for superpixel A: A, AB; ABC; ABD; ABCD; AC; ACD; and AD. Furthermore, referring to FIG. 3B, in which superpixel D is the current superpixel, superpixels A, C, and G would be considered for possible local combination with superpixel D. Thus, each of the following unique local combinations may be considered for superpixel D: D, DA; DAC; DAG; DACG; DC; DCG; and DG. However, if superpixel D is the current superpixel after superpixel A was the current superpixel, in order to increase efficiency, combinations DA and DAC may be skipped, since these combinations are redundant to combinations AD and ACD, which were considered when superpixel A was the current superpixel.

In step 160, a score is determined for each possible local combination for the current superpixel (i.e., by itself or with one or more other superpixels within search radius R). In an embodiment, the score represents the relative likelihood that a particular local combination of superpixel(s) represents an object (e.g., nucleus) of interest. For example, in an embodiment, a local combination of superpixel(s) with a lower score is less likely to represent an object of interest than a local combination of superpixel(s) with a higher score. However, it should be understood that in an alternative embodiment, lower scores may be used to represent a higher likelihood that local combinations of superpixel(s) represent an object of interest, and higher scores may be used to represent a lower likelihood that local combinations of superpixel(s) represent an object of interest.

Figure 2B:
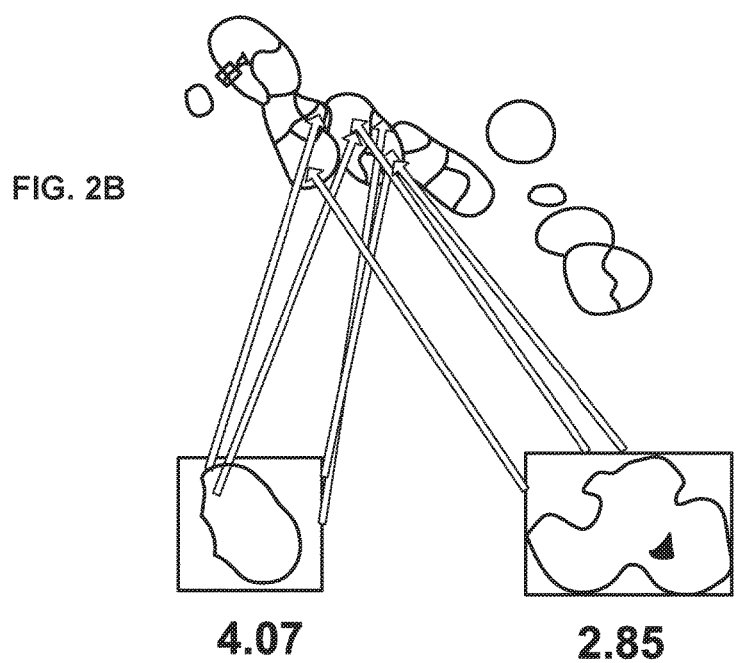
FIG. 2B illustrates an example of how combinations of superpixels may be scored, according to an embodiment.

FIG. 2B illustrates an example of how combinations of superpixels may be scored, according to an embodiment for nuclear segmentation. As illustrated, a first possible combination of four superpixels yields a score of 4.07, whereas a second possible combination of three superpixels yields a score of 2.85. Accordingly, in this example, the first possible combination is more likely to represent a nucleus of interest than the second possible combination. Notably, the first combination is more circular than the second combination, and the second combination comprises a gap. Thus, it is intuitive that the first combination should score higher than the second combination, since it more closely resembles the shape of a typical nucleus.

Each local combination of superpixel(s) may be scored based on a likelihood metric that quantifies the likelihood that a particular local combination represents an object (e.g., nucleus) of interest. The "local score" for each local combination may comprise the likelihood metric, consist of the likelihood metric, or be derived from the likelihood metric.

In an embodiment, the likelihood metric comprises the Dice Index. The Dice index may be computed as:

$$D = \frac{2|M \cap A|}{|M| + |A|},$$

wherein M represents the set of pixels composing a manually-annotated nucleus, A represents the automatically detected set of pixels corresponding to that nucleus, and M∩A is the set intersection of M and A. The Dice Index ranges in value from zero (representing no overlap between A and M) to one (representing perfect overlap between A and M).

Alternatively, other measures of shape similarity, such as the Hausdorff Distance, or a combination of different measures, may be used as the likelihood metric. In any case, the likelihood metric for any particular local combination of superpixel(s) may be computed against the annotated object (e.g., nucleus), with which it shares the most overlap, from the set of annotated test images. If no such object exists, a local score of zero may be assigned to the particular local combination.

In an embodiment, the likelihood metric may be multiplied by the number of superpixels in the particular local combination to obtain a local score representing the overall likelihood that the local combination of superpixel(s) represents an object (e.g., nucleus) of interest from the set of annotated test images. For example, in an embodiment which utilizes the Dice Index as the likelihood metric, the local score for a local combination with a Dice Index of 4.00 and consisting of four superpixels may be computed as 16.00 (i.e., 4.00×4).

In an embodiment, the local score for each combination of superpixels in the set of annotated test images, computed in step 160, is used to train a random forest regression algorithm or other regression or machine-learning algorithm to predict the local score (e.g., based on the Dice Index or other likelihood metric) for any local combination of superpixel(s). This prediction may be based on a series of geometric or numerical features computed for the local combination. For example, a feature vector may be generated for each local combination. Each feature vector may comprise a plurality of values representing geometric attributes (e.g., circularity, normalized moment, etc.) of the local combination. It should be understood that, in alternative embodiments, other machine-learning algorithms may be employed, such as support vector machines, neural networks, etc. In addition, the machine-learning algorithm may be applied to raw pixels of a local combination of superpixel(s), rather than geometric or numerical features.

In an embodiment, the geometrical features that are used to train the machine-learning algorithm are translational, rotational, and scale-invariant features. Specifically, these features may comprise a convexity defects score, an eccentricity, an isoperimetric quotient, an obtuse ratio, a solidity, a squareness, and/or the seven invariant Hu moments. The convexity defects score may be defined as:

$$C = e^{-d},$$

where d is the number of convexity defects.

Convexity defects may be computed as the deviations between the local combination and its convex hull. Eccentricity may be computed as:

$$E = \sqrt{1 - b^2/a^2},$$

wherein a and b represent the lengths of the semi-major axis and the semi-minor axis, respectively, of the ellipse that best fits the local combination. The isoperimetric quotient may be defined as:

$$Q = 4\pi A/p2,$$

wherein A is the area of the local combination and P is its perimeter. Obtuse ratio may be computed as the ratio of obtuse angles to the total angles in the local combination. Solidity may be defined as the ratio of the area of its local combination to the area of its convex hull. Squareness may be computed as:

$$S = A/D^2,$$

wherein A is the area of the local combination, and D is the longest dimension of the bounding box enclosing the local combination. The seven invariant Hu moments may be computed as described, in an embodiment, in "Visual pattern recognition by moment invariants," by Hu, IRE Transactions on Information Theory (1962), pp. 179-87, which is hereby incorporated herein by reference. In an embodiment, prior to training and prediction, all of the features are scaled and centered by subtracting the mean and dividing by the standard deviation.

Once the machine-learning algorithm has been trained, it may be used in step 160 to predict a local score for any possible local combination of superpixel(s) in a digital image. Thus, for example, if the digital image received in step 110 is a digital image to be processed (e.g., rather than to train the machine-learning algorithm), via the loop comprised of steps 150 and 160, each possible local combination for the current superpixel is scored. Referring to FIG. 3A, in an embodiment in which only superpixels that are wholly within search radius R are considered, each of the local combinations of A, AB, ABC, ABC, ABCD, AC, ACD, and AD would be scored in step 160. Referring to FIG. 3B, in an embodiment in which only superpixels that are wholly within search radius R are considered, each of the local combinations of D, DAG, DACG, DC, DCG, and DG would be scored in step 160. Note that in this case, it is assumed that superpixel A was considered before superpixel D, and therefore, local combinations DA and DAC are skipped in steps 150 and 160, since they are redundant to local combinations AD and ACD, respectively, which were considered in a prior iteration of steps 150 and 160.

Advantageously, the machine learning techniques described above consider local combinations that would not be considered by techniques which rely on measures of similarity between superpixels. For instance, by using a search radius R, rather than a similarity measure, the disclosed techniques will consider combinations between the current superpixel and surrounding superpixels (possibly including non-adjacent superpixels), regardless of whether or not those superpixels are similar or dissimilar to the current superpixel. Accordingly, in contrast to conventional processes, the disclosed process does not suffer from the possibility that two superpixels representing a single object (e.g., nucleus) may fail to be properly combined due to a dissimilarity between their features.

1.3. Global Optimization

As discussed above, in an embodiment, the local score determined, in step 160, for each possible local combination, represents the likelihood that the local combination is an object (e.g., nucleus) of interest (e.g., as in a likelihood metric, such as the Dice Index, multiplied by the number of superpixels in the combination). When process 100 transitions from step 140 to step 170, a local score has been assigned to each of these local combinations of superpixels.

In step 170, an optimization technique, such as integer programming, may be used to identify a globally optimum set of local combinations. In an embodiment, each global set of local combinations consists of all of the superpixels remaining after step 130, but differs from each of the other possible global sets in how those superpixels are joined into local combinations of superpixels.

FIGS. 4A-4D illustrate a simplified example of global sets of local combinations of superpixels, according to an embodiment. For ease of explanation, FIGS. 4A-4D depict a digital image with only four superpixels: A; B; C; and D. However, it should be understood that, for an actual digital image, there may any multitude of superpixels, including thousands, millions, or billions of superpixels. Regardless of the number of pixels and superpixels, the described embodiments may be scaled to cover any number of pixels and superpixels. In addition, for the purposes of illustration, FIGS. 4A-4D will be described according to an embodiment in which all superpixels, that are at least partially within a search radius R of the current superpixel, are considered for local combination with the current superpixel.

Figure 4A:
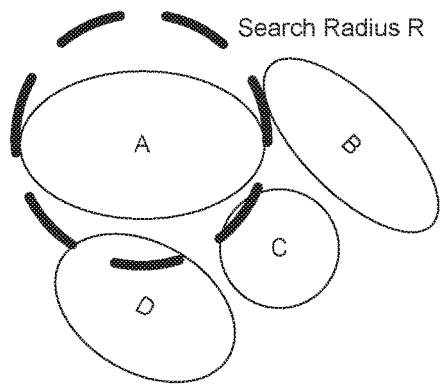
FIGS. 4A-4D illustrate a simplified example of how global sets of local superpixel combinations may be determined, according to an embodiment.

In FIG. 4A, a first iteration of the outer loop formed by steps 140-160 is performed. Specifically, superpixel A is selected as the current superpixel in step 140. In iterations of the inner loop formed by steps 150 and 160, the local combination of A is selected in step 150 and scored in step 160, then the local combination of AC is selected in step 150 and scored in step 160, then the local combination of AD is selected in step 150 and scored in step 160, and then the local combination of ACD is selected in step 150 and scored in step 160.

Figure 4B:
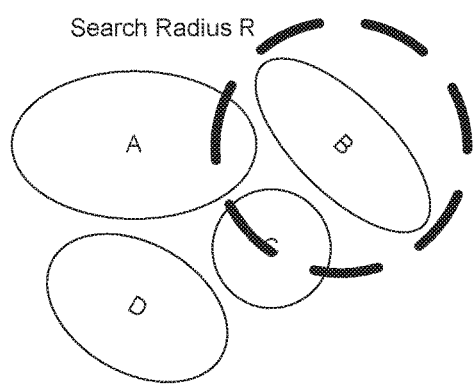

In FIG. 4B, a second iteration of the outer loop formed by steps 140-160 is performed. Specifically, superpixel B is selected as the current superpixel in step 140. In iterations of the inner loop formed by steps 150 and 160, the local combination of B is selected in step 150 and scored in step 160, then the local combination of BA is selected in step 150 and scored in step 160, then the local combination of BC is selected in step 150 and scored in step 160, and then the local combination of BAC is selected in step 150 and scored in step 160.

Figure 4C:
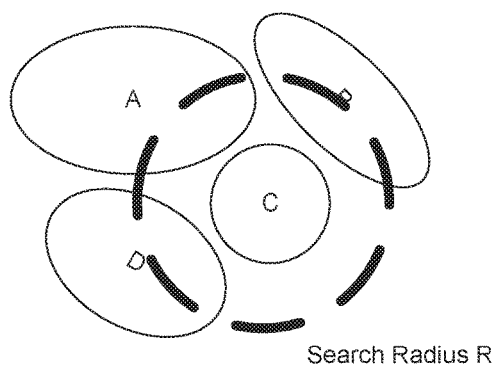

In FIG. 4C, a third iteration of the outer loop formed by steps 140-160 is performed. Specifically, superpixel C is selected as the current superpixel in step 140. In iterations of the inner loop formed by steps 150 and 160, the local combination of C is selected in step 150 and scored in step 160, then the local combination of CD is selected in step 150 and scored in step 160, then the local combination of CBD is selected in step 150 and scored in step 160, and then the local combination of CABD is selected in step 150 and scored in step 160. The local combinations of CA, CB, CAB, and CAD may be skipped, since AC, BC, BAC, and ACD have already been scored, as described above.

Figure 4D:
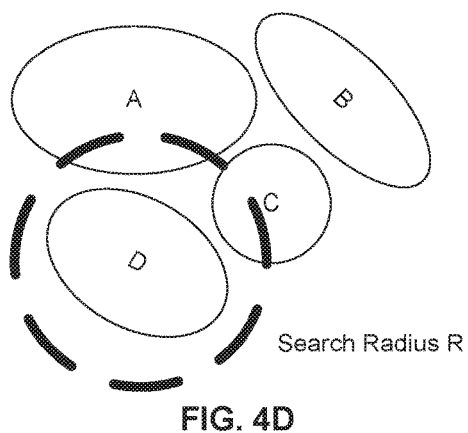

In FIG. 4D, a fourth iteration of the outer loop formed by steps 140-160 is performed. Specifically, superpixel D is selected as the current superpixel in step 140. In the inner loop formed by steps 150 and 160, only local combination D is selected in step 150 and scored in step 160, since all other possible local combinations (i.e., DA, DC, and DAC) have already been scored (i.e., as AD, CD, and ACD), as discussed above.

Next, process 100 proceeds to step 170 with local scores for each of the local combinations of A, B, C, D, AC, AD, ACD, BA, BC, BAC, CD, CBD, and CABD, which for ease of understanding below may be relabeled as A, B, C, D, AB, AC, AD, BC, CD, ABC, ACD, BCD, and ABCD. It should be understood that if the local score, determined in step 160, is zero for any of these local combinations (i.e., indicating that there is no possibility that the local combination represents an object of interest), that local combination may be discarded, such that it will not be considered in the global sets of local combinations in step 170.

In an embodiment, the possible global sets of local combinations are restricted such that each global set may only consist of local combinations that, collectively, include any particular superpixel no more than k times, where k is an integer greater than zero. Parameter k may be a system-specified or user-specified (e.g., input by a user via a user interface) parameter. By default, k may be one, in which case, each global set may include each superpixel only once.

In the illustrated example in FIGS. 4A-4D, if k is one, the possible global sets consist of: A-B-C-D; A-BC-D; A-B-CD; A-BCD; AB-C-D; AB-CD; AC-B-D; AD-B-C; AD-BC; ABC-D; ACD-B; and ABCD. For comparison, if k is two, the possible global sets increase to include, for example, A-AB-CD (k=2 allows superpixel A to be included in two local combinations), ABC-ACD (k=2 allows superpixels A and C to be included in two local combinations), ACD-BC, and so forth. Generally, k should be a small integer that represents the expected maximum number of overlapping nuclei. If the detection of overlapping nuclei is not desired, then k should be set to one.

In addition, the global sets of local combinations may be restricted such that each global set must comprise local combinations that, collectively, include each superpixel (i.e., remaining after step 130) at least one time. In this case, if k is one, then each global set must comprise local combinations that, collectively, include every particular superpixel exactly one time.

In step 170, a global score may be determined for global sets of local combinations. In an embodiment, the global score is derived from the local scores for all of the local combination(s) in the global set. For example, the global score for the global set of A-BC-D may be derived from a first local score for the local combination of A, a second local score for the local combination of BC, and/or a third local score for the local combination of D. The global score may be a straight sum of all of the local scores for the local combinations within the global set. In such a case, the global score for the global set of A-BC-D would be the sum of the first local score (i.e., for A), the second local score (i.e., for BC), and the third local score (i.e., for D). Accordingly, if the first local score was 2.91, the second local score was 0.95, and the third local score was 2.11, the global score for A-BC-D would be 5.97.

In an embodiment, step 170 may be implemented using integer programming. In integer programming, a function of the local combinations of superpixels is maximized by assigning each local combination a value of zero or one, indicating whether or not the local combination is to be used in the solution, and calculating a global score based on (e.g., by summing) the local scores for the local combinations that are assigned a value of one. The result is a set of assignments, representing a global set of local combinations, that produces a maximum global score. An example of branch-and-cut integer programming, which may be used in an embodiment, is described in "Branch-and-Cut Algorithms for Combinatorial Optimization Problems," by John E. Mitchell, Handbook of Applied Optimization (2002), pp. 65-77, which is hereby incorporated herein by reference. However, in other embodiments, other integer programming techniques may be used, such as branch-and-bound, and other optimization techniques may be used, such as simulated annealing.

The use of integer programming ensures that the set of local combinations is selected in such a way as to obtain a globally optimal solution to an objective function, subject to two sets of constraints. The objective function to be maximized is the sum of local combination scores. The first set of constraints is that each superpixel must be assigned to at least one and at most k local combinations. In an embodiment of the algorithm, k=1, which means that object (e.g., nuclei) overlap is not allowed. However, in other embodiments, k can be set to a value greater than one to allow overlapping objects (e.g., nuclei). This constraint can be expressed for any superpixel i as:

$$\sum_{j=1}^{M} b_{ij} = 1,$$

wherein $b_{ij}$ is a binary variable which is equal to one if superpixel i is assigned to local combination j, and equal to zero otherwise. The second set of constraints is that the set of binary variables belonging to the same global set must be all equal to zero or all equal to one at the same time. This prevents assigning only part of a local combination to the final solution. Mathematically, this can be expressed as:

$$b_{ij} = b_{mj} \forall i, m \in \text{combination}_j.$$

Other optimization methods such as genetic programming or simulated annealing may be used to achieve the same purpose, which is the maximization of the global segmentation score.

Table 1 below illustrates example results of a global score determination performed on the global sets of the superpixels illustrated in FIGS. 4A-4D, using example local scores for each local combination scored in step 160, in an embodiment in which a current superpixel is combined with all superpixels that are at least partially within radius R, k=1, and each superpixel must appear at least once in each global set (i.e., each superpixel must appear exactly once in each global set):

TABLE 1

| local score | A 2.91 | B 6.73 | C 0.76 | D 2.11 | AB 0.26 | AC 3.88 | AD 4.13 | BC 0.95 | CD 1.87 | ABC 1.36 | ACD 7.94 | BCD 0.49 | ABCD 8.01 | global score |
|---|---|---|---|---|---|---|---|---|---|---|---|---|---|---|
| A-B-C-D | 1 | 1 | 1 | 1 | 0 | 0 | 0 | 0 | 0 | 0 | 0 | 0 | 0 | 12.51 |
| A-BC-D | 1 | 0 | 0 | 1 | 0 | 0 | 0 | 1 | 0 | 0 | 0 | 0 | 0 | 5.97 |
| A-B-CD | 1 | 1 | 0 | 0 | 0 | 0 | 0 | 0 | 1 | 0 | 0 | 0 | 0 | 11.51 |
| A-BCD | 1 | 0 | 0 | 0 | 0 | 0 | 0 | 0 | 0 | 0 | 0 | 1 | 0 | 3.40 |
| AB-C-D | 0 | 0 | 1 | 1 | 1 | 0 | 0 | 0 | 0 | 0 | 0 | 0 | 0 | 3.13 |
| AB-CD | 0 | 0 | 0 | 0 | 1 | 0 | 0 | 0 | 1 | 0 | 0 | 0 | 0 | 2.13 |
| AC-B-D | 0 | 1 | 0 | 1 | 0 | 1 | 0 | 0 | 0 | 0 | 0 | 0 | 0 | 12.72 |
| AD-B-C | 0 | 1 | 1 | 0 | 0 | 0 | 1 | 0 | 0 | 0 | 0 | 0 | 0 | 11.62 |
| AD-BC | 0 | 0 | 0 | 0 | 0 | 0 | 1 | 1 | 0 | 0 | 0 | 0 | 0 | 5.08 |
| ABC-D | 0 | 0 | 0 | 1 | 0 | 0 | 0 | 0 | 0 | 1 | 0 | 0 | 0 | 3.47 |
| ACD-B | 0 | 1 | 0 | 0 | 0 | 0 | 0 | 0 | 0 | 0 | 1 | 0 | 0 | 14.67 |
| ABCD | 0 | 0 | 0 | 0 | 0 | 0 | 0 | 0 | 0 | 0 | 0 | 0 | 1 | 8.01 |

In step 170, the global set of local combinations having the optimum global score is identified. The optimum score may be the maximum score in embodiments in which higher scores indicate a higher likelihood that the local combinations within a particular global set accurately represent object(s) of interest. It should be understood that, in alternative embodiments, the local score for each local combination and/or the calculation of a global score may be modified such that lower global scores represent higher likelihoods that the local combinations within a particular global set accurately represent object(s) of interest, in which case the global set of local combinations with the minimum global score should be determined as having the optimum global score in step 170. In either case, the global set of local combinations identified in step 170 is the global set that has the highest likelihood of accurately segmenting the superpixels in the digital image into local combinations which accurately represent objects (e.g., nuclei) of interest. Consequently, each local combination of superpixels comprised in the global set identified in step 170 may be assumed to represent an object (e.g., nucleus) of interest for subsequent visualization and/or analysis.

In the example illustrated in Table 1, the global set of ACD-B, comprising two local combinations of ACD and B, would be identified in step 170 as the globally optimum set (i.e., with a global score of 14.67). Thus, the global set of ACD-B would be determined by process 100, in step 170, to have a higher likelihood of representing accurate object (e.g., nuclei) identification than any of the other global sets. The global set of ACD-B delineates the superpixels, A, B, C, and D into a first object (e.g., nucleus) comprising superpixels A, C, and D, and a second object (e.g., nucleus) comprising only superpixel B. This delineation of objects (e.g., nuclei) may be input into any subsequent application which has use for such information. For example, if the subsequent application comprises an object-counting (e.g., nucleus-counting) algorithm, the algorithm would output a count of two (i.e., the first object represented by superpixels ACD, and the second object represented by superpixel B).

Advantageously, the described process of global optimization, represented by step 170 in process 100, produces an optimal segmentation. In contrast, a process which merely selects local combinations having the highest local scores may produce suboptimal segmentation. For example, referring to Table 1, the global combination of ABCD has the highest score among local combinations. However, the selection of global combination of ABCD, based on it having the highest score among local combinations, would result in a suboptimal segmentation, since global combinations with higher overall scores exist (e.g., ACD-B, discussed above).

1.4. Applications

Once the global set having the optimum global score is identified, each local combination in that global set may be determined to be a separate object (e.g., nucleus). In other words, the perimeter of each local combination represents the perimeter of an individual object within the digital image. Accordingly, the objects in the digital image received in step 110 may be delineated, for example, by assigning a unique label $L_i$ to each object. Each superpixel within a given object may be assigned the same label $L_i$, such that the superpixels are grouped together according to the respective objects that they represent. In an embodiment, the object (e.g., nucleus) may be visually distinguished within the digital image, for example, using boundary lines, labels, or other annotations.

Figure 2C:
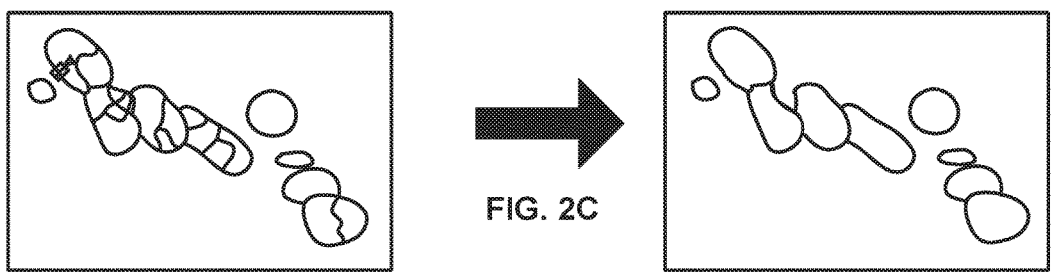
FIG. 2C illustrates an example of global optimization, according to an embodiment.

FIG. 2C illustrates an example of global optimization, according to an embodiment. In the illustrated embodiment, the sum of Dice Indices for the local combinations of superpixels have been maximized over the entire digital image. As illustrated, the combination of superpixels assigned to each local combination (i.e., representing a predicted nucleus) in the maximized global set are visually annotated as a single nucleus in the final segmented digital image.

Alternatively or additionally, the delineation of objects, represented by the global set of local combinations of superpixels identified in step 170, may be input into further applications for analysis. For example the same methodology may be used to assign cells to one of normal or malignant tissue. In this case, the superpixels will be at the cell level, and the objects will be at the tissue level. At a lower scale, the methodology may be used to assign fluorescently-labeled signals to specific cell compartments.

2. Example Processing Device

Figure 5:
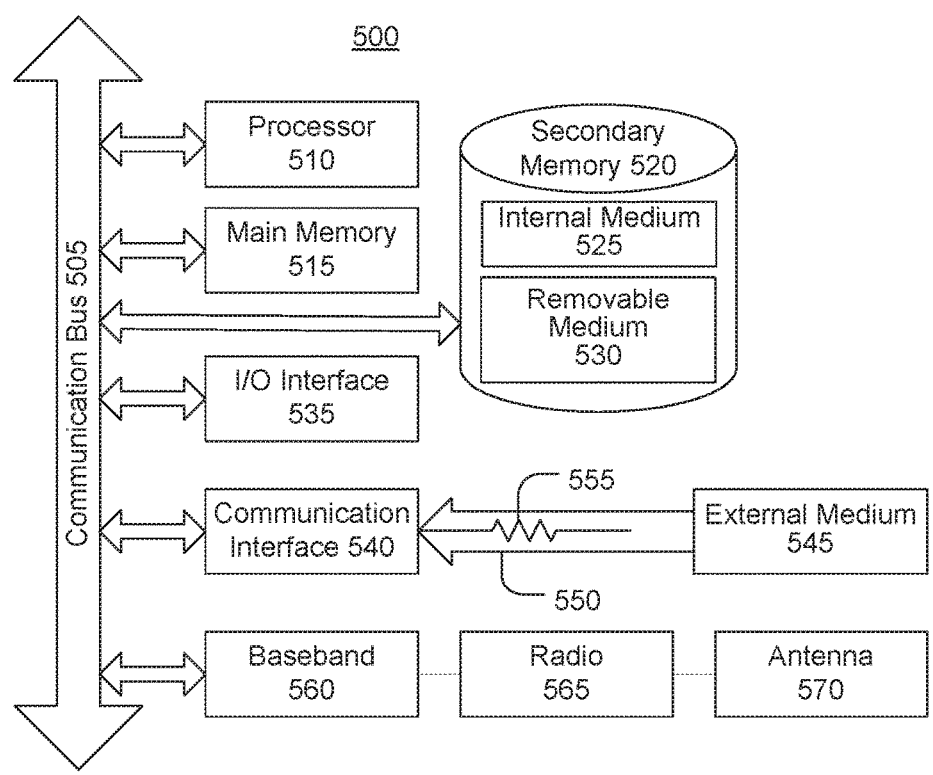
FIG. 5 illustrates a processing system on which one or more of the processes described herein may be executed, according to an embodiment.

FIG. 5 is a block diagram illustrating an example wired or wireless system 500 that may be used in connection with various embodiments described herein. For example, system 500 may be used as or in conjunction with one or more of the processes described above, such as process 100 in FIG. 1, and may represent components of a system that executes one or more of the processes described above, such as process 100 in FIG. 1. System 500 can be a server or any conventional personal computer, or any other processor-enabled device that is capable of wired or wireless data communication. Other computer systems and/or architectures may be also used, including devices that are not capable of wired or wireless data communication, as will be clear to those skilled in the art.

System 500 preferably includes one or more processors, such as processor 510. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 510. Examples of processors which may be used with system 500 include, without limitation, the Pentium® processor, Core i7® processor, and Xeon® processor, all of which are available from Intel Corporation of Santa Clara, Calif.

Processor 510 is preferably connected to a communication bus 505. Communication bus 505 may include a data channel for facilitating information transfer between storage and other peripheral components of system 500. Communication bus 505 further may provide a set of signals used for communication with processor 510, including a data bus, address bus, and control bus (not shown). Communication bus 505 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 500 preferably includes a main memory 515 and may also include a secondary memory 520. Main memory 515 provides storage of instructions and data for programs executing on processor 510, such as one or more of the functions and/or modules discussed above. It should be understood that programs stored in the memory and executed by processor 510 may be written and/or compiled according to any suitable language, including without limitation C/C++, Java, JavaScript, Perl, Visual Basic, .NET, and the like. Main memory 515 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 520 may optionally include an internal memory 525 and/or a removable medium 530. Removable medium 530 is read from and/or written to in any well-known manner. Removable storage medium 530 may be, for example, a magnetic tape drive, a compact disc (CD) drive, a digital versatile disc (DVD) drive, other optical drive, a flash memory drive, etc.

Removable storage medium 530 is a non-transitory computer-readable medium having stored thereon computer-executable code (i.e., software) and/or data. The computer software or data stored on removable storage medium 530 is read into system 500 for execution by processor 510.

In alternative embodiments, secondary memory 520 may include other similar means for allowing computer programs or other data or instructions to be loaded into system 500. Such means may include, for example, an external storage medium 545 and a communication interface 540, which allows software and data to be transferred from external storage medium 545 to system 500. Examples of external storage medium 545 may include an external hard disk drive, an external optical drive, an external magneto-optical drive, etc. Other examples of secondary memory 520 may include semiconductor-based memory such as programmable read-only memory (PROM), erasable programmable read-only memory (EPROM), electrically erasable read-only memory (EEPROM), or flash memory (block-oriented memory similar to EEPROM).

As mentioned above, system 500 may include a communication interface 540. Communication interface 540 allows software and data to be transferred between system 500 and external devices (e.g. printers), networks, or other information sources. For example, computer software or executable code may be transferred to system 500 from a network server via communication interface 540. Examples of communication interface 540 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device. Communication interface 540 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 540 are generally in the form of electrical communication signals 555. These signals 555 may be provided to communication interface 540 via a communication channel 550. In an embodiment, communication channel 550 may be a wired or wireless network, or any variety of other communication links. Communication channel 550 carries signals 555 and can be implemented using a variety of wired or wireless communication means including wire or cable, fiber optics, conventional phone line, cellular phone link, wireless data communication link, radio frequency ("RF") link, or infrared link, just to name a few.

Computer-executable code (i.e., computer programs or software) is stored in main memory 515 and/or the secondary memory 520. Computer programs can also be received via communication interface 540 and stored in main memory 515 and/or secondary memory 520. Such computer programs, when executed, enable system 500 to perform the various functions of the disclosed embodiments as described elsewhere herein.

In this description, the term "computer-readable medium" is used to refer to any non-transitory computer-readable storage media used to provide computer-executable code (e.g., software and computer programs) to system 500. Examples of such media include main memory 515, secondary memory 520 (including internal memory 525, removable medium 530, and external storage medium 545), and any peripheral device communicatively coupled with communication interface 540 (including a network information server or other network device). These non-transitory computer-readable mediums are means for providing executable code, programming instructions, and software to system 500.

In an embodiment that is implemented using software, the software may be stored on a computer-readable medium and loaded into system 500 by way of removable medium 530, I/O interface 535, or communication interface 540. In such an embodiment, the software is loaded into system 500 in the form of electrical communication signals 555. The software, when executed by processor 510, preferably causes processor 510 to perform the features and functions described elsewhere herein.

In an embodiment, I/O interface 535 provides an interface between one or more components of system 500 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

System 500 also includes optional wireless communication components that facilitate wireless communication over a voice network and/or a data network. The wireless communication components comprise an antenna system 570, a radio system 565, and a baseband system 560. In system 500, radio frequency (RF) signals are transmitted and received over the air by antenna system 570 under the management of radio system 565.

In one embodiment, antenna system 570 may comprise one or more antennae and one or more multiplexors (not shown) that perform a switching function to provide antenna system 570 with transmit and receive signal paths. In the receive path, received RF signals can be coupled from a multiplexor to a low noise amplifier (not shown) that amplifies the received RF signal and sends the amplified signal to radio system 565.

In alternative embodiments, radio system 565 may comprise one or more radios that are configured to communicate over various frequencies. In an embodiment, radio system 565 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 565 to baseband system 560.

If the received signal contains audio information, then baseband system 560 decodes the signal and converts it to an analog signal. Then the signal is amplified and sent to a speaker. Baseband system 560 also receives analog audio signals from a microphone. These analog audio signals are converted to digital signals and encoded by baseband system 560. Baseband system 560 also codes the digital signals for transmission and generates a baseband transmit audio signal that is routed to the modulator portion of radio system 565. The modulator mixes the baseband transmit audio signal with an RF carrier signal generating an RF transmit signal that is routed to antenna system 570 and may pass through a power amplifier (not shown). The power amplifier amplifies the RF transmit signal and routes it to antenna system 570 where the signal is switched to the antenna port for transmission.

Baseband system 560 is also communicatively coupled with processor 510, which may be a central processing unit (CPU). Processor 510 has access to data storage areas 515 and 520. Processor 510 is preferably configured to execute instructions (i.e., computer programs or software) that can be stored in main memory 515 or secondary memory 520. Computer programs can also be received from baseband processor 560 and stored in main memory 510 or in secondary memory 520, or executed upon receipt. Such computer programs, when executed, enable system 500 to perform the various functions of the disclosed embodiments. For example, data storage areas 515 or 520 may include various software modules.

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method comprising using at least one hardware processor to:
   determine a plurality of superpixels in a digital image;
   for each of the plurality of superpixels,
      identify any superpixels located within a search radius from the superpixel, and,
      for each unique local combination between the superpixel and any identified superpixels located within the search radius from the superpixel, determine a local score for the local combination; and
   identify one of a plurality of global sets of local combinations with an optimum global score based on the determined local scores.

2. The method of claim 1, wherein determining the plurality of superpixels in the digital image comprises:
   receiving the digital image; and
   combining a plurality of pixels in the digital image into an initial set of superpixels; and
   determining the plurality of superpixels from the initial set of superpixels.

3. The method of claim 2, wherein determining the plurality of superpixels from the initial set of superpixels comprises selecting the plurality of superpixels from the initial set of superpixels based on a threshold.

4. The method of claim 1, wherein each of the plurality of global sets of local combinations comprises each of the superpixels at least once.

5. The method of claim 4, wherein each of the plurality of global sets of local combinations consists of each of the superpixels exactly once.

6. The method of claim 1, wherein identifying one of the plurality of global sets of local combinations with an optimum global score comprises maximizing a sum of the local scores for all local combinations within each of the plurality of global sets.

7. The method of claim 6, wherein maximizing the sum of the local scores for all local combinations within each of the plurality of global sets is performed by integer programming.

8. The method of claim 1, wherein a superpixel is located within the search radius when it is at least partially within the search radius.

9. The method of claim 1, wherein a superpixel is located within the search radius only when it is wholly within the search radius.

10. The method of claim 1, wherein the local score for each local combination is based on a Dice Index for the local combination.

11. The method of claim 10, wherein the local score for each local combination comprises the Dice Index for the local combination multiplied by a number of superpixels within the local combination.

12. The method of claim 1, wherein the local score for each local combination represents a likelihood that the local combination represents an object of interest.

13. The method of claim 12, further comprising using the at least one hardware processor to visually distinguish each object of interest within the digital image within a user interface.

14. The method of claim 12, wherein the object of interest is a cell nucleus.

15. A system comprising:
   at least one hardware processor; and
   one or more software modules that, when executed by the at least one hardware processor,
      determine a plurality of superpixels in a digital image,
      for each of the plurality of superpixels, identify any superpixels located within a search radius from the superpixel, and, for each unique local combination between the superpixel and any identified superpixels located within the search radius from the superpixel, determine a local score for the local combination, and
      identify one of a plurality of global sets of local combinations with an optimum global score based on the determined local scores.

16. A non-transitory computer-readable medium having instructions stored thereon, wherein the instructions, when executed by a processor, cause the processor to:
   determine a plurality of superpixels in a digital image;
   for each of the plurality of superpixels,
      identify any superpixels located within a search radius from the superpixel, and,
      for each unique local combination between the superpixel and any identified superpixels located within the search radius from the superpixel, determine a local score for the local combination; and
   identify one of a plurality of global sets of local combinations with an optimum global score based on the determined local scores.

17. The method of claim 12, further comprising using the at least one hardware processor to:
   group each local combination of superpixels in the identified global set into a single object of interest; and
   classify each object of interest into one of a plurality of categories.

18. The method of claim 17, wherein each object of interest is at least a portion of a tissue cell, and wherein the plurality of categories comprise normal tissue and malignant tissue.

* * * * *